US006421455B1

(12) United States Patent
Rosén et al.

(10) Patent No.: US 6,421,455 B1
(45) Date of Patent: Jul. 16, 2002

(54) METHOD FOR DETECTING CANCER ON SKIN OF HUMANS AND MAMMALS AND ARRANGEMENT FOR PERFORMING THE METHOD

(75) Inventors: Arne Rosén, Partille; Olle Larkö, Göteborg; Ann-Marie Wennberg, Göteborg; Fredrik Gudmundsson, Göteborg; Leif Johansson, Göteborg, all of (SE)

(73) Assignee: Medeikonos AB (SE)

(*) Notice: Subject to any disclaimer, the term of this patent is extended or adjusted under 35 U.S.C. 154(b) by 0 days.

(21) Appl. No.: 09/254,035

(22) PCT Filed: Aug. 11, 1997

(86) PCT No.: PCT/SE97/01336
§ 371 (c)(1),
(2), (4) Date: Jul. 6, 1999

(87) PCT Pub. No.: WO98/09155
PCT Pub. Date: Mar. 5, 1998

(30) Foreign Application Priority Data

Aug. 27, 1996 (SE) ............................................. 9603095

(51) Int. Cl.[7] .................................................. G06K 9/00
(52) U.S. Cl. ...................................................... 382/133
(58) Field of Search ................................ 382/128, 129, 382/133, 181, 190, 191, 312, 313, 321; 424/1.41, 9.6, 9.8, 9.81, 62, 63, 155.1; 800/10; 600/556; 607/901; 356/300, 302, 303

(56) References Cited

U.S. PATENT DOCUMENTS

| 4,029,085 A | * | 6/1977 | Dewitt et al. | 600/315 |
| 4,786,813 A | * | 11/1988 | Svanberg et al. | 250/461.1 |
| 4,930,516 A | * | 6/1990 | Alfano et al. | 600/477 |
| 5,422,093 A | * | 6/1995 | Kennedy et al. | 424/9.61 |

FOREIGN PATENT DOCUMENTS

| GB | 2203831 | 10/1988 | G01N/21/64 |
| WO | 9101727 | 2/1991 | A61K/31/195 |
| WO | 9313403 | 7/1993 | G01N/21/64 |

\* cited by examiner

*Primary Examiner*—Andrew W. Johns
*Assistant Examiner*—Shervin Nakhjavan
(74) *Attorney, Agent, or Firm*—Orum & Roth

(57) ABSTRACT

The invention relates to a method for detecting cancer on skin of humans and mammals by picturing spectroscopy. The method includes that delta aminolevulimic acid ALA is applied on the skin on that area where cancer is suspected to be present, the substance is removed after 1 to 24 hours, and the area is illumiated with light having a wave-length of 330–440 nm and the fluorescent irradiation which arises is registered and evaluated, which radiation has a wave-length 610–715 nm. The invention also includes an arrangement for performing the method.

19 Claims, 2 Drawing Sheets

Figure 1:
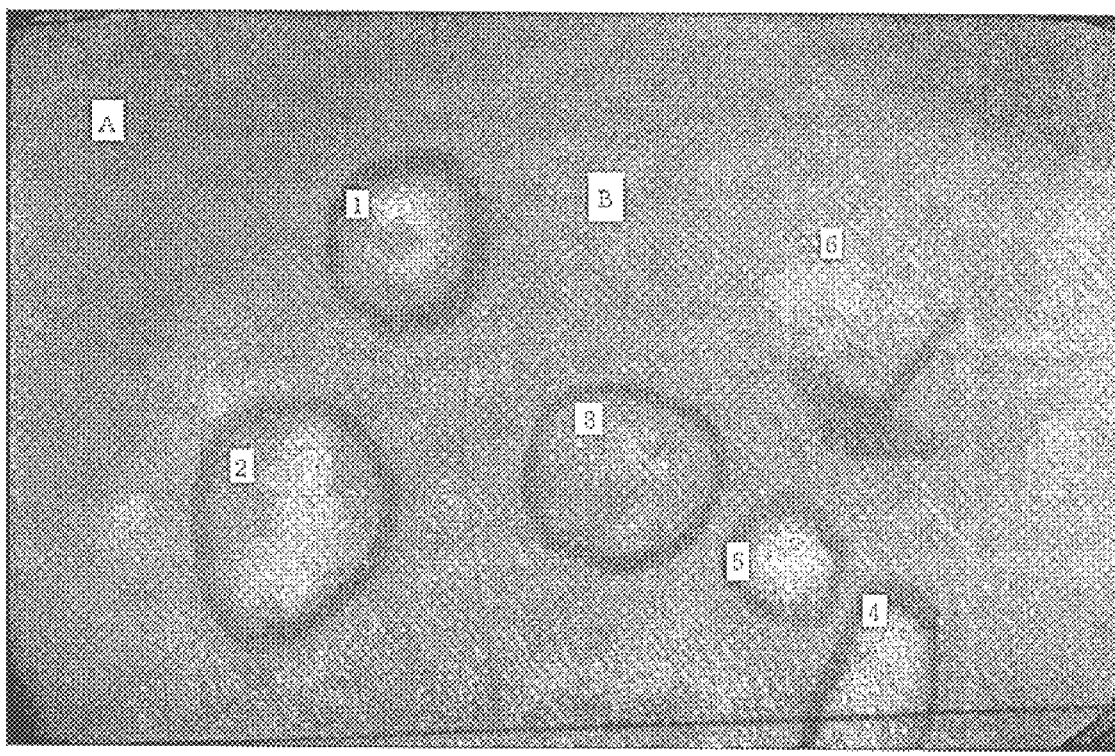

METHOD FOR DETECTING CANCER ON SKIN OF HUMANS AND MAMMALS AND ARRANGEMENT FOR PERFORMING THE METHOD

TECHNICAL FIELD

The present invention relates to a method for detecting cancer on skin of humans and mammals by imaging spectroscopy. Spectroscopy can be performed in that a chemical agent is collected on or in the cancer cells which agent makes a fluorescent irradiation having a certain wave-length when it is illuminated with normal light or a certain wave-length. The invention also includes an arrangement for performing the method.

PRIOR ART

It is well known that cancer can have many different shapes both within the body and on the skin. Also skin cancer can be divided in different categories such as basiloma, squamous cell carcinoma and malignant melanoma. From these mentioned kinds the latter is the most serious one, whereas the first mentioned is the least serious one and results in complications only when this type of cancer is located on special sensible parts of the body, such as on the eyelid, the nose or the like.

When for example basiloma cancer is developed, the surgeon will simply cut away the sick part and a piece outside this so that he will be sure that all has been cut away. On some places such as on an eyelid it is not possible to cut away too much and the surgeon then will first cut away that area in which he with certainty can see is attacked whereafter he will cut away strips of the surrounding skin area and these strips will be microscopically investigated to control that the whole attacked area has been taken away. It may become necessary to cut out many strips and such an operation can take many hours in that the investigation of the strips takes its time. This operation method is called Moh's surgery.

When a cancer tumour or a cancer stain has developed, so that it is visible, no detection method is needed to find it. However, it is of vital importance that cancer in a development stadium which cannot be seen with the eye also can be detected so that early measures can be applied. For this purpose it is known to use for example spectroscopy which means that the area where cancer can be suspected to be present is illuminated and fluorescent light which is irradiated from the illuminated area and which comes from the agents which has been collected in or around the cancer cells are detected. Such an agent can be a derivative of haematoporphyrin which consists of different porphyrines and which is injected in the blood. After injection of this agent the illumination is delayed until the haematoporphyrin derivative has disappeared from the healthy tissues which does not occur in cancer attacked tissues where these derivatives instead are collected. The illumination occurs preferably with laser light. Besides that it is possible to detect the cancer cells by the irradiated fluorescent light the cancer is also treated by applying such a strong light that oxygen in status nascendi is formed so that the cells are killed. This method and the production of haematoporphyrin is described in the U.S. Pat. No. 5,015,463. A similar method and an apparatus for detection is described in the Swedish patent 84 05 276-0.

It is also possible to detect sickly changes in the body without the use of any chemical agent and only by means of a mapping of the irradiated fluorescent light which is created by means of a light source. When light containing different wave-lengths is applied an auto-fluorescence is namely created from healthy tissue in the body and this can then be mapped. At sick areas the fluorescent picture is changed and the sick area can therefore be located. The light source at such an investigation is preferably laser light. The system and apparatus are disclosed in the American patent U.S. Pat. No. 5,345,941.

A method for detection of cancer is described in WO 93/13403. Here delta aminolevulinic acid is applied to the skin and the ratio between the specific peak of fluorescence intensity in red and in blue-green is used for the detection when the excitation is made the ultra violet, violet, or blue wave range.

The Technical Problem

With the first method of Moh's surgery the apparent disadvantage of the treatment is that it takes very long time and creates suffering for the patient and is also costly. This operation is therefore performed only at very few areas.

With the second method when haematoporphyrin is injected the problem is that the heamatoporphyrin derivative is not an agent of the some persons and that also a long time has to lapse before this agent has disappeared from the healthy tissues before the examination can be started.

The third method with mapping the auto fluorescence without help of any contrasting agent, color or the like is complicated and not reliable and requires also a very expensive equipment.

The Solution

It has therefore for long been a desire to be able to discover skin cancer at a very early stage in a reliable way without injecting substances not belonging to the body in a quick way and with a speedy and inexpensive apparatus and according to the invention one has therefore brought about a method for detecting cancer on skin of humans and mammals by imaging spectroscopy which is characterized in that a composition containing delta amino levulinic acid (ALA) first is applied on that area of the skin where cancer is suspected to be present and is allowed to stay there for 1 to 24 hours whereupon the skin area which has been influenced with ALA after removing the composition is illuminated with light having a wave-length of 363–367 nm and 404–408 nm and an intensity of 0,1–10 mW/cm$^2$ and that during the illumination arising fluorescent irradiation having a wave-length of 610–715 nm from the area which is radiated with light is registered and evaluated.

It is according to the invention suitable that the registration of the fluorescent irradiation occurs by photographing with a camera preferably of the type CCS (Charge Coupled Device) on which a filter which is blocking all light having a wave-length shorter than 610 nm is applied.

According to the invention it is suitable that the composition consists of ALA in concentration of 5–25% in an oil-in-water or water-in-oil, emulsion.

The illumination with light is according to the invention created by a mercury lamp which after filtering (with filter BG12) gives light within the described area.

The invention includes also use of an apparatus for performing the method and comprises a source of light in the form of a mercury lamp for creating, normal noncoherent light, a filter (BG12) for filtering of the light created by the light source which filter allows light with a wave-length of 363–367 nm and 404–408 to penetration, a registration device for registering of fluorescent light having a wave-length of 610–715 nm from the skin area which has been illuminated with the created and filtered light and a composition containing delta amino levulinic acid for application on the skin area which is intended to be examined.

The registering equipment according to the invention consists suitably of a camera preferably of the type CCD (Charge Coupled Device) on which a filter which blocks all light having a wave-length lower than 610 nm has been applied.

The composition according to the invention consists suitably of an oil-in-water or a water-in-oil emulsion containing 5–12% ALA.

FIGURE DESCRIPTION

Figure 2:
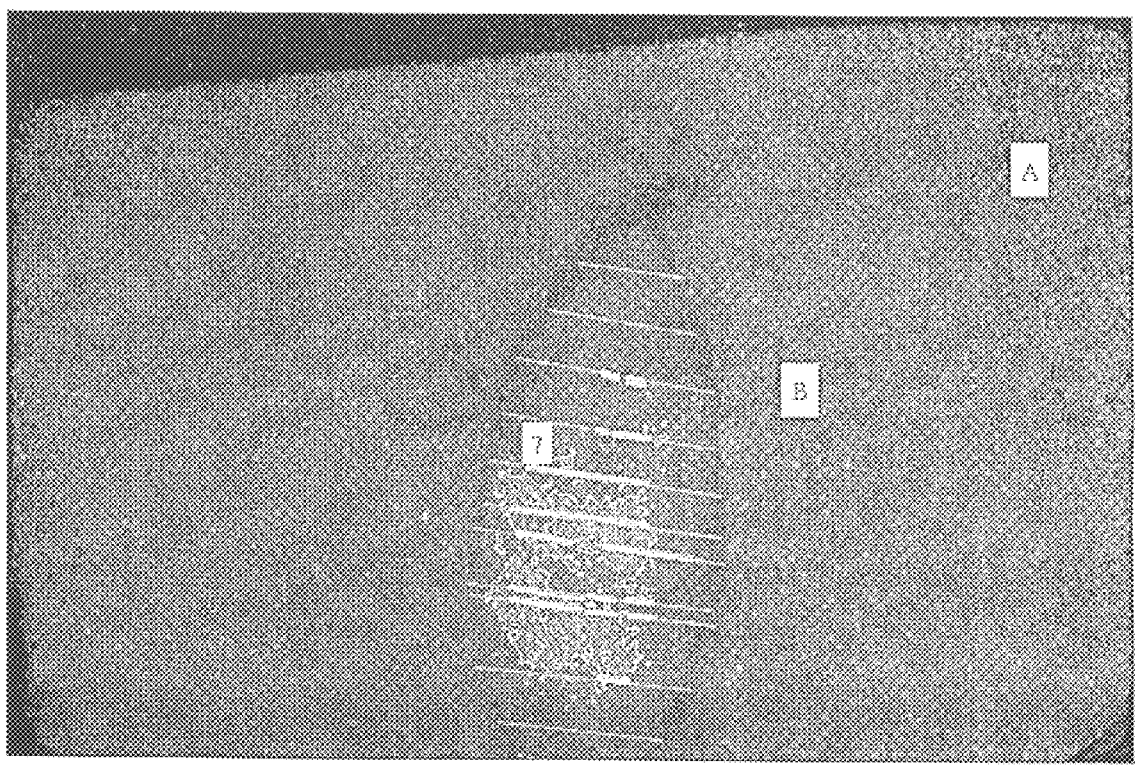

The invention will in the following be described more in detail in connection with the attached photographic figures where FIG. 1 show a photograph of a skin area having cancer stains and where FIG. 2 show another area of skin having cancer stains and detection stains according to the present invention.

DETAILED DESCRIPTION

The method according to the invention is carried out in the way that first a water-in-oil emulsion or an oil-in-water emulsion is prepared form a compound called delta amino levulinic acid (ALA) having an ALA concentration of 5–25%. ALA is present in the form of powder and is easily solved in water. This agent which has the formula I is normally produced in the body in the bone tissue of the spinal cord and is a building stone for the haemoglobin.

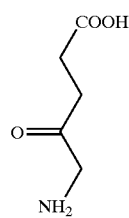

I

Through a series of biochemical reactions a substance is built which is called protoporphyrin IX, having the formula II.

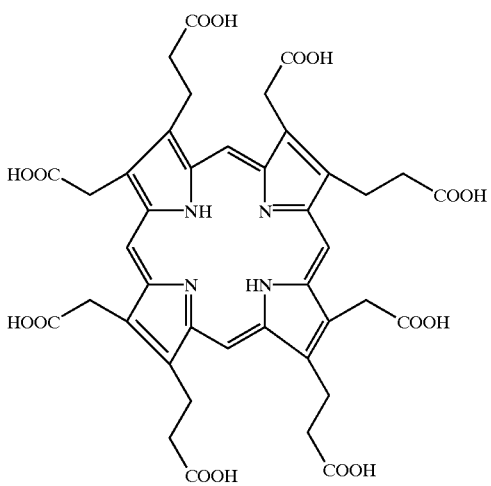

II

This protoporphyrin molecule is the pre-stage of the haemoglobin and it lacks principly only three-valent iron in relation to this.

When the emulsion or the gel with ALA is put on the skin the preformation of protoporphyrin will go quickly and this composition will be collected in a very high degree on or in the sick cancer cells. The patient himself can put on this gel at home before he or she goes to the hospital with the presumption that the gel is allowed to be on the skin area for at least about 5 hours. This time is not critical, it may sometimes suffice with one hour, but a longer period of time up to 24 hours may also occur. It is suitable that this actual skin area on which the ALA gel has been applied is occluded with a plastic film.

When the detection of cancer cells is to be started the ALA gel is removed in a suitable way and the skin area which is suspected to comprise cancer cells is illuminated with a normal non-coherent light with a wave-length of 330–440 nm which is the range of wave-length where protoporphyrin IX has a strong absorption. This light should be even over the whole surface which is to be examined. Even though normal light is preferred it is also possible to use laser light.

The suitable wave-length of the light is obtained by illuminating with preferably a mercury lamp and by filtrating away the light which has a longer wave-length than about 440 nm and shorter than 330 nm. The filter may consist of a long-pass filter of the type BG12. The intensity of the incoming light may suitably be 0,1–10 mW/cm². In this filtrated light from the mercury lamp intensity peaks occur in the area of 363–367 nm and 404–408 n.

With this illumination the protoporphyrin which is an agent of the body itself fluoresces. It has been concentrated at the cancer-sick place by the ALA lotion and it will fluoresce within the wave-length area of 610–715 nm. This irradiation can be registered by photographing suitably with a CCD camera (Charge Couple Device) on which a filter which blocks all light having a shorter wave-length than 610 nm suitably has been mounted. It is suitable to let the picture be visible on a screen or the like. The exposing time which is required is less than 2 s. More pictures can be taken to give a safer diagnosis. The entire examination takes accordingly only a few minutes.

It is especially a beginning cancer which can be detected in this way. When the cancer has been developed so that it is visible the picture obtained in the above way will be less sharp for different reasons. This is, however, not any disadvantage with the method since the cancer is visible anyway. The reason for this phenomenon is presumably that small bleedings or the like disturb the collection of protoporphyrin or the emission of the fluorescent rays.

The FIGS. 1 and 2 show pictures taken on two different patients where the cancer areas are shown. The intensity of the exciting light was about 0,5 mW/cm$^2$ and the exposing time was 2 s.

FIG. 1 shows the fluorescent picture on the back of a 65 year old man. The intensity of the fluorescence is shown in a grey scale where the lighter areas emit more fluorescence than the darker areas. The width of the pictured area is 11,3 cm and the height 7,5 cm. The black circles and the black arrow are lines which are made on the skin with a pen. The darker area A is skin which has not been treated with ALA and the average fluorescence is called skin auto fluorescence. This fluorescence arises when incoming light excites the molecules normally being present in the skin. The lighter area B is skin which has been treated with ALA without any tumours having been detected. The average fluorescence level within the area B is 1,9 ×the fluorescence within the area A. A white contour having a higher level of fluorescence is shown around the areas with an intensity which is 2,75 ×the skin auto fluorescence. These areas 1–4 are tumours which have been diagnosed with existing technique. The skin around the tumours 1 and 3 had to a great extent been destroyed by tumours. This may be an explanation that the fluorescence is low in the centre of the area 1 and around the area 3.

The areas 5 and 6 could however not be identified as tumours in a usually way by existing technique but could only be detected by means of the technique according to the present invention. Small pieces of skin were cut out from these apparently healthy areas 5 and 6 and laboratory analysis of these pieces showed that the areas 5 and 6 also contained tumours.

FIG. 2 shows a fluorescence picture from the breast of a 45 year old woman. The intensity of the fluorescence is represented in a grey scale where the lighter areas emit more fluorescence than the darker areas. The width of the pictured area is 5,2 cm and the height 3,5 cm. The black lines and the crosses on the skin has been made with a pen. The darker areas A is skin without any ALA treatment and the fluorescence is called skin auto fluorescence. The lighter area B is skin which has been treated with ALA without any detection of tumours. The average level for the fluorescence in this area B is 2,0 ×the fluorescence in the area A. Levels having a white contour have arisen around the areas having higher intensity than 2,75 ×the skin auto fluorescence. The tumour from the part in the centre of the area 7 is identified as an area of an earlier healed wound from an earlier made biopsy which had confirmed tumour. The area within the black line was cut out with conventional surgery technique. The skin piece was prepared chemically and cut for microscopically analysis for determining of the extension of the tumour. The thin grey lines show the cut. The thick white lines show the presence of tumour tissue along this cut. As appears the conventional microscope analysis coincides mainly with the pictured spectroscopy.

By the present invention a method for detecting of skin cancer which is very reliable, quick, a few minutes, which does not add substances which are not present in the body and which can be performed with a simple and cheap apparatus has been created.

The invention is not limited to the embodiment described but can be varied in different ways within the scope of the claims.

What is claimed is:

1. Method for detecting cancer on skin of humans and mammals by imaging spectroscopy, including a composition containing delta amino levulic acid ALA first being applied on the area of the skin where cancer is suspected to be present and is there allowed to stay for 1 to 24 hours, whereupon the skin area having been influenced by ALA is illuminated after removing the composition, wherein the illuminating light has a wave-length of 363–367 nm and 404–408 nm and an intensity of 0.1–10 mW/cm$^2$ and that during the illumination arising fluorescent irradiation having a wave-length of 610–715 nm from the area having been illuminated is registered and evaluated.

2. Method according to claim 1, wherein the registration of the fluorescent irradiation occurs by photographing with a camera preferably of the type CCD (Charged Couple Device).

3. Method according to claim 2, wherein all light having a shorter wave-length than 610 nm is filtrated away.

4. Method according to claim 3, wherein the composition consists of ALA in a concentration of 5–25% in an oil-in-water or water-in-oil emulsion.

5. Method according to claim 2, wherein the composition consists of ALA in a concentration of 5–25% in an oil-in-water or water-in-oil emulsion.

6. Method according to claim 2, wherein the illumination with light is made with a mercury lamp with after filtering (with filter BG12) gives light within the desired area.

7. Apparatus according to claim 6, wherein a filter for filtering away light having a shorter wave-length than 610 nm.

8. Use of an apparatus for performing the method according to claim 2, comprising a light source in the form of a mercury lamp for creating usually non-coherent light, a filter (BG12) for filtering the light coming from the light source which filter allows light with a wave-length of 363–367 nm and 404–408 nm to penetrate, a registration device for registering fluorescent light having a wave-length of 610–715 nm from the skin area which is illuminated with the created and filtered light and a composition containing delta amino levulic acid for application on the skin area which is intended to be examined.

9. Method according to claim 3, wherein the illumination with light is made with a mercury lamp with after filtering (with filter BG12) gives light within the desired area.

10. Method according to claim 1, wherein the composition consists of ALA in a concentration of 5–25% in an oil-in-water or water-in-oil emulsion.

11. Method according to claim 1, wherein the illumination with light is made with a mercury lamp with after filtering (with filter BG12) gives light within the desired area.

12. Use of an apparatus for performing the method according to claim 1, comprising a light source in the form of a mercury lamp for creating usually non-coherent light, a filter (BG12) for filtering the light coming from the light source which filter allows light with a wave-length of 363–367 nm and 404–408 nm to penetrate, a registration device for registering fluorescent light having a wave-length of 610–715 nm from the skin area which is illuminated with the created and filtered light and a composition containing delta amino levulic acid for application on the skin area which is intended to be examined.

13. Use of an apparatus according to claim 12, wherein the registration device is a camera preferably of the type CCD (Charge Coupled Device).

14. Use of an apparatus according to claim 13, wherein a filter for filtering away light having a shorter wave-length than 610 nm.

15. Use of an apparatus according to claim 12, wherein the composition consists of an oil-in-water or a water-in-oil emulsion containing 5–25% ALA.

16. Use of an apparatus according to claim 13, wherein the composition consists of an oil-in-water or a water-in-oil emulsion containing 5–25% ALA.

17. Apparatus for detecting cancer on skin of humans and mammals by imaging spectroscopy, using a composition containing delta amino levulic acid for application on the skin area which is intended to be examined, comprising a light source, wherein said light source having the form of a mercury lamp for creating usually non-coherent light, a filter (BG12) for filtering the light coming from the light source, which filter allows light with a wave-length of 363–367 nm and 404–408 nm to penetrate, and a registration device for registering fluorescent light having a wave-length of 610–715 nm from the skin area which is illuminated with the created and filtered light.

18. Apparatus according to claim 5, wherein the registration device is a camera preferably of the type CCD (Charge Coupled Device).

19. Apparatus according to claim 5 wherein in a filter for filtering away light having a shorter wave-length than 610 nm.

\* \* \* \* \*